United States Patent
Shirono

(10) Patent No.: US 10,426,353 B2
(45) Date of Patent: Oct. 1, 2019

(54) PHOTOACOUSTIC APPARATUS, SIGNAL PROCESSING METHOD, AND STORAGE MEDIUM STORING PROGRAM

(71) Applicant: CANON KABUSHIKI KAISHA, Tokyo (JP)

(72) Inventor: Jumpei Shirono, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 798 days.

(21) Appl. No.: 14/565,140

(22) Filed: Dec. 9, 2014

(65) Prior Publication Data
US 2015/0164338 A1     Jun. 18, 2015

(30) Foreign Application Priority Data
Dec. 17, 2013 (JP) ................................ 2013-260681

(51) Int. Cl.
*A61B 5/00* (2006.01)
*A61B 5/145* (2006.01)

(52) U.S. Cl.
CPC ........ *A61B 5/0095* (2013.01); *A61B 5/14542* (2013.01)

(58) Field of Classification Search
CPC .......................... A61B 5/0095; A61B 5/14542
See application file for complete search history.

(56) References Cited

U.S. PATENT DOCUMENTS

| | | | | |
|---|---|---|---|---|
| 8,326,567 B2 * | 12/2012 | Masumura | ........... | A61B 5/0091 702/127 |
| 9,554,709 B2 * | 1/2017 | Fukutani | ........... | A61B 5/0095 |
| 2010/0070233 A1 * | 3/2010 | Masumura | ........... | A61B 5/0091 702/127 |
| 2010/0087733 A1 * | 4/2010 | Nakajima | ........... | A61B 5/0073 600/437 |
| 2010/0094561 A1 * | 4/2010 | Masumura | ........... | A61B 5/0073 702/19 |
| 2011/0172513 A1 * | 7/2011 | Nakajima | ........... | A61B 5/0059 600/407 |
| 2014/0046165 A1 * | 2/2014 | Fukutani | ........... | A61B 5/0095 600/407 |

(Continued)

FOREIGN PATENT DOCUMENTS

JP     WO 2012144395 A1 *   10/2012   ........... A61B 5/0095

OTHER PUBLICATIONS

C. Li; L. V. Wang; "Photoacoustic tomography and sensing in biomedicine", Phys. Med. Biol. 54 (2009) R59-R97.

(Continued)

*Primary Examiner* — Angela M Hoffa
(74) *Attorney, Agent, or Firm* — Canon U.S.A., Inc. IP Division

(57) ABSTRACT

An apparatus includes a reception unit configured to receive a photoacoustic wave generated when an object is irradiated with light and output a received signal, and a processing unit configured to obtain an initial acoustic pressure distribution in the object by using the received signal and obtain object information by using an equation representing propagation of the light which includes the initial acoustic pressure distribution and a correction term including a background absorption coefficient distribution of the object.

16 Claims, 14 Drawing Sheets

(56) References Cited

U.S. PATENT DOCUMENTS

| | | | |
|---|---|---|---|
| 2014/0296690 A1* | 10/2014 | Miyasato | A61B 5/0095 600/407 |
| 2017/0042429 A1* | 2/2017 | Nakajima | A61B 5/0095 |
| 2017/0100039 A1* | 4/2017 | Fukutani | A61B 5/0095 |
| 2017/0164880 A1* | 6/2017 | Umezawa | A61B 5/14552 |
| 2017/0168150 A1* | 6/2017 | Fukutani | G01S 7/52053 |
| 2017/0172420 A1* | 6/2017 | Nakamura | A61B 5/7278 |
| 2017/0215739 A1* | 8/2017 | Miyasato | A61B 5/14542 600/309 |
| 2017/0215740 A1* | 8/2017 | Nakajima | G01N 21/1702 600/407 |

OTHER PUBLICATIONS

D. Contini, et.al; "Photon migration through a turbid slab described by amodel based on diffusion approximation. I. Theory", Appl. Otpics; Jul. 1, 1997 / vol. 36, No. 19 ; 4587-4599.

\* cited by examiner

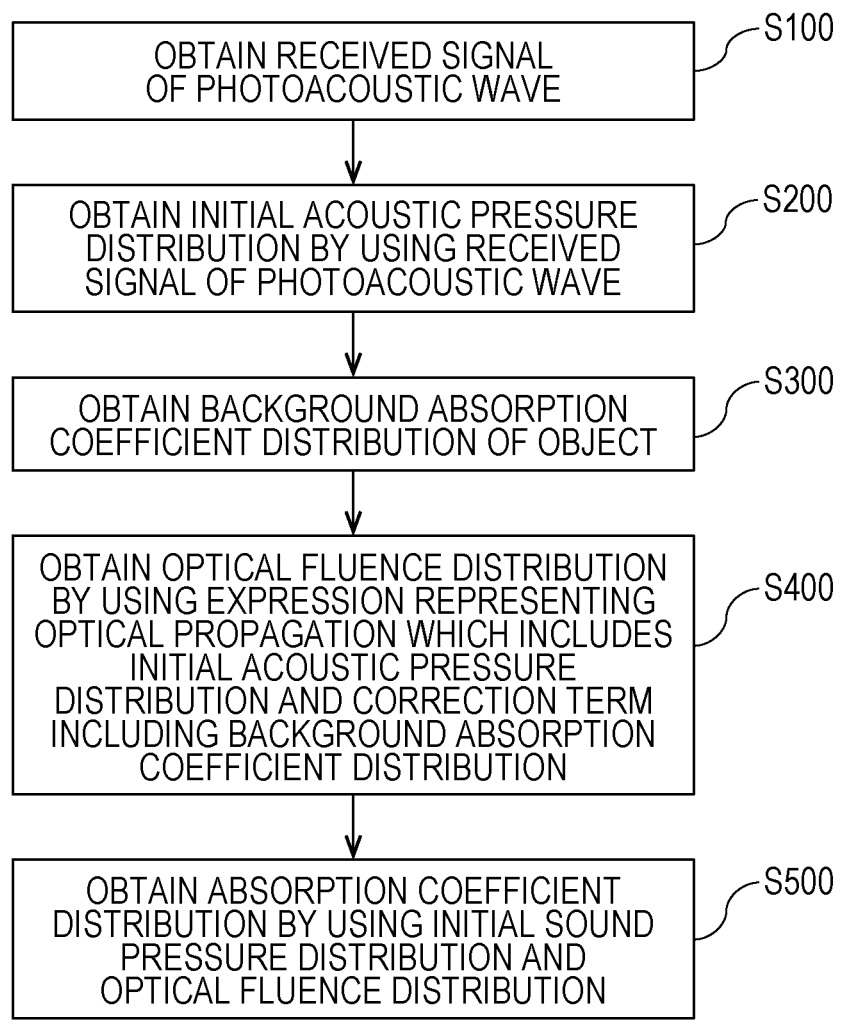

FIG. 9
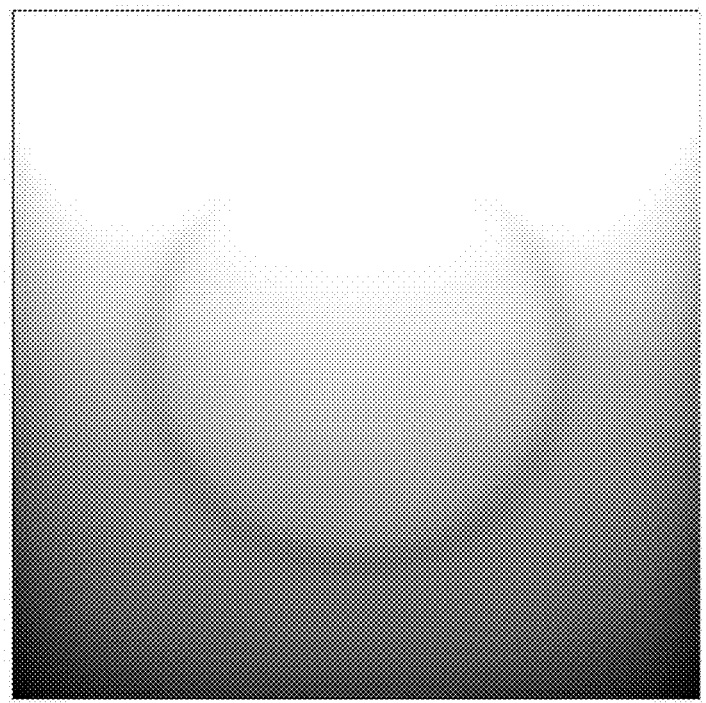
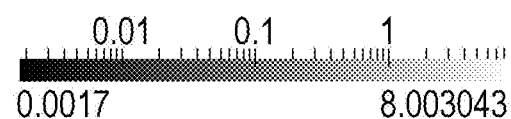

FIG. 10
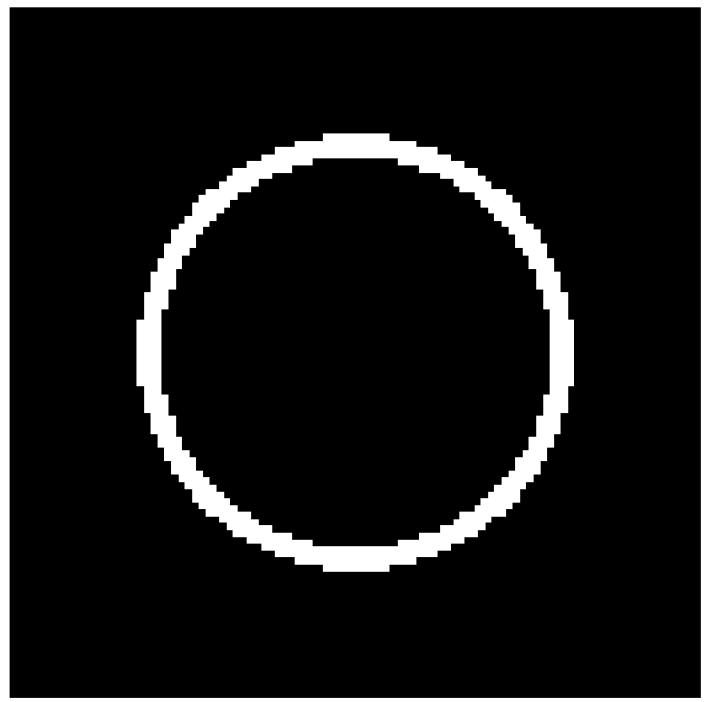
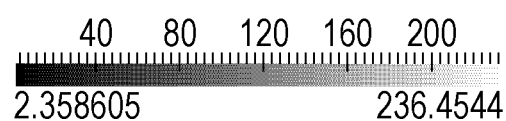

FIG. 11
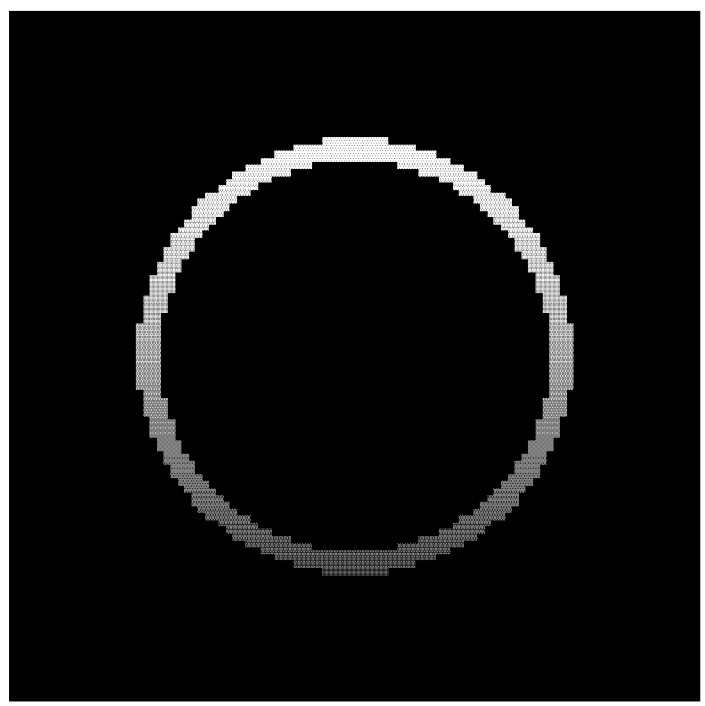
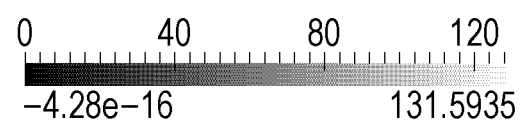

FIG. 14
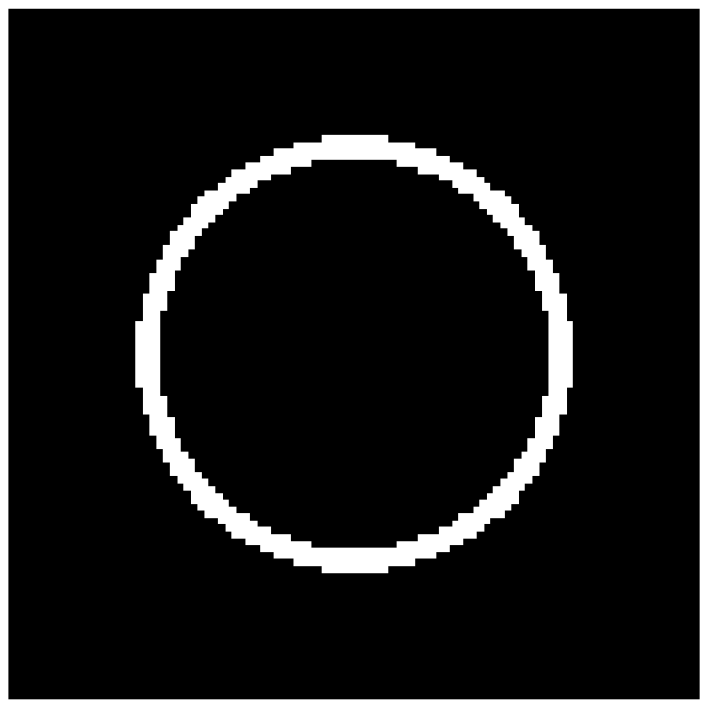
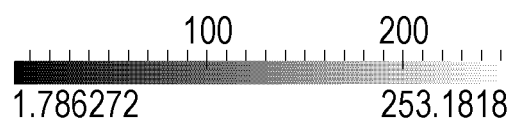

PHOTOACOUSTIC APPARATUS, SIGNAL PROCESSING METHOD, AND STORAGE MEDIUM STORING PROGRAM

BACKGROUND OF THE INVENTION

Field of the Invention

The present invention relates to a photoacoustic apparatus that receives a photoacoustic wave generated when an object is irradiated with light and obtains object information, a signal processing method, and a storage medium storing a program.

Description of the Related Art

When an object such as a living matter is irradiated with light, the light propagated and diffused in the object is absorbed, and a pressure is generated, so that a photoacoustic wave is generated. In recent years, an apparatus using this photoacoustic effect has been actively researched and developed. In particular, photo-acoustic imaging (PAI) has attracted attention in which the generated photoacoustic waves are received from various directions, and analysis processing of the received photoacoustic waves is performed, so that a spatial distribution of object information in the object can be obtained.

Among the object information obtained by the PAI, an absorption coefficient distribution is much anticipated. The optical absorption is mainly derived from hemoglobins (oxyhemoglobin, deoxyhemoglobin) in blood vessels, and if the absorption coefficient distribution is measured while a wavelength of the light is changed, it is possible to obtain concentration distributions of the respective hemoglobins. In addition, it is possible to obtain a ratio of oxygenated hemoglobin in total hemoglobin, that is, an oxygen saturation distribution on the basis of the concentration distributions of the respective hemoglobins. To accurately obtain the above-described object information, the absorption coefficient distributions in the respective wavelengths are accurately obtained.

Hereinafter, a method of obtaining the absorption coefficient distribution will be described. To facilitate understanding, first, phenomena that actually occur will be explained in order, and next, a method of obtaining the absorption coefficient distribution will be described so as to trace back the phenomena. As mention above, the photoacoustic effect is a phenomenon where an object is irradiated with light, the light is propagated and diffused, the light is absorbed, a pressure is generated, and a photoacoustic wave is generated. It is known that propagation and diffusion of the light at visible to near-infrared wavelengths in the living matter except for an extremely shallow part can be satisfactorily approximated by an optical diffusion equation, and an optical diffusion equation in a stationary state can be written as in Expression (1).

$$-\nabla \cdot \{D(\vec{r})\nabla\phi(\vec{r})\} + \mu_a(\vec{r})\phi(\vec{r}) = s(\vec{r}) \quad (1)$$

Where D denotes a diffusion coefficient distribution, $\phi$ denotes an optical fluence distribution in the object, $\mu_a$ denotes an absorption coefficient distribution in the object (real absorption coefficient distribution), s denotes a source term of the light, and r denotes a position. The pressure, the absorption coefficient, and the optical fluence have a relationship as represented in Expression (2).

$$p_0(\vec{r}) = \Gamma(\vec{r})\mu_a(\vec{r})\phi(\vec{r}) \quad (2)$$

Where $p_0$ denotes a real initial acoustic pressure distribution, and $\Gamma$ denotes a Gruneisen coefficient distribution. This generated photoacoustic wave at the real initial acoustic pressure $p_0$ propagates through the object to be measured by an acoustic wave receiver.

The absorption coefficient distribution is obtained so as to trace back this. First, a time variation of the acoustic pressure of the photoacoustic wave propagating through the object is measured, and the acoustic pressure distribution generated in the object is obtained from the measurement result by a method as described in C. Li, L. V. Wang, "Photoacoustic tomography and sensing in biomedicine", Phys. Med. Biol. 54 (2009) R59, which will be referred to as Non-patent document 1. This distribution will be referred to as initial acoustic pressure distribution $\delta p_0$.

If the initial acoustic pressure distribution $\delta p_0$ is considered as the real initial acoustic pressure distribution $p_0$, an absorption coefficient distribution $\mu_a$ can be obtained by dividing the initial acoustic pressure distribution $\delta p_0$ by the optical fluence distribution $\phi$ and the Gruneisen coefficient distribution $\Gamma$ on the basis of Expression (2). However, as may be understood from this procedure, to obtain the absorption coefficient distribution $\mu_a$ from the initial acoustic pressure distribution $\delta p_0$, the optical fluence distribution $\phi$ is to be obtained. In view of the above, the optical fluence distribution $\phi$ is obtained by using Expression (1). For example, $\mu_a\phi$ in Expression (1) is transformed into $p_0/\Gamma$ on the basis of Expression (2) to form Expression (3).

$$-\nabla \cdot \{D(\vec{r})\nabla\phi(\vec{r})\} + p_0(\vec{r})/\Gamma(\vec{r}) = s(\vec{r}) \quad (3)$$

Therefore, if the initial acoustic pressure distribution $\delta p_0$ is considered as the real initial acoustic pressure distribution $p_0$, that is, considered as Expression (4), Expression (4) can be solved with respect to the optical fluence distribution $\phi$ to be obtained.

$$-\nabla \cdot \{D(\vec{r})\nabla\phi(\vec{r})\} + \delta p_0(\vec{r})/\Gamma(\vec{r}) = s(\vec{r}) \quad (4)$$

In this manner, by solving the optical propagation equation including the initial acoustic pressure distribution $\delta p_0$, it is possible to obtain the optical fluence distribution $\phi$.

SUMMARY OF THE INVENTION

An apparatus disclosed in the present invention includes a reception unit configured to receive a photoacoustic wave generated when an object is irradiated with light and output a received signal, and a processing unit configured to obtain an initial acoustic pressure distribution in the object by using the received signal and obtain object information by using an equation representing propagation of the light which includes the initial acoustic pressure distribution and a correction term including a background absorption coefficient distribution of the object.

Further features of the present invention will become apparent from the following description of exemplary embodiments with reference to the attached drawings.

BRIEF DESCRIPTION OF THE DRAWINGS

FIG. 3 illustrates an operation flow of the photoacoustic apparatus according to the first exemplary embodiment.

FIG. 9 illustrates the optical fluence distribution obtained according to Example 1.

FIG. 10 illustrates an absorption coefficient distribution according to Example 1.

FIG. 11 illustrates an absorption coefficient distribution obtained according to a comparison example.

FIG. 14 illustrates an absorption coefficient distribution obtained according to Example 2.

DESCRIPTION OF THE EMBODIMENTS

Figure 1:
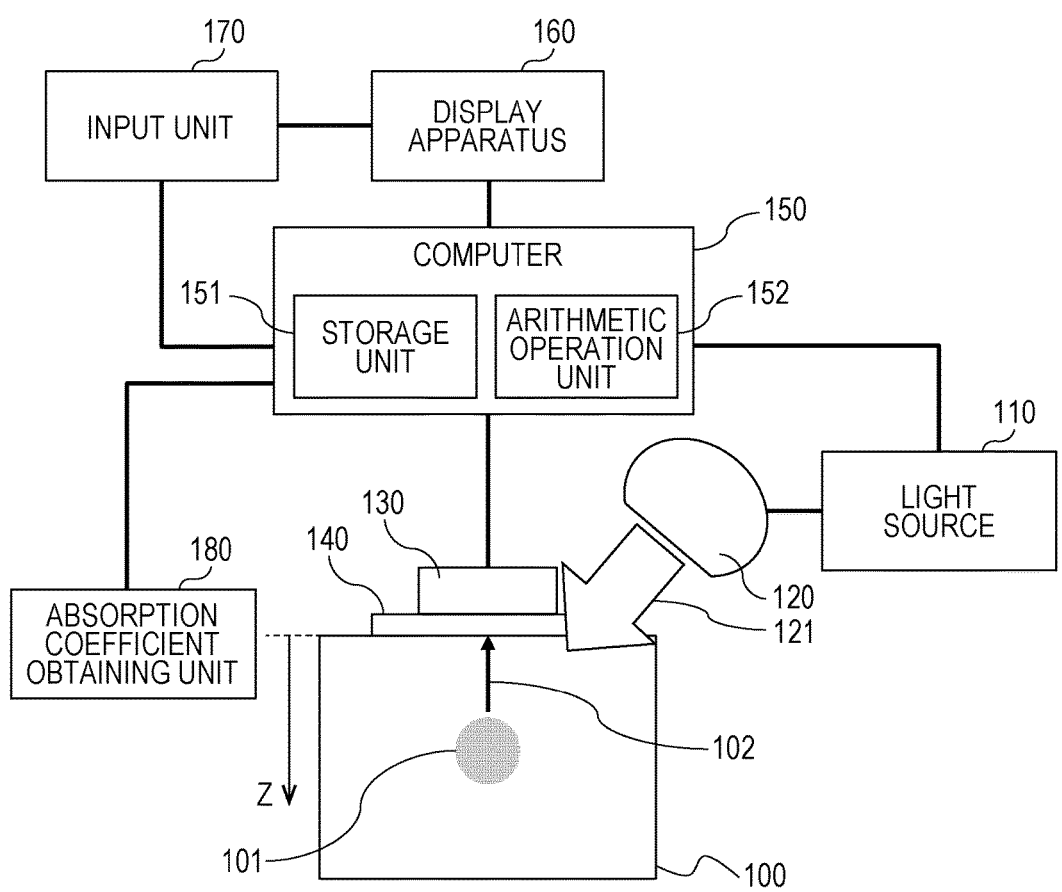
FIG. 1 is a schematic diagram of a photoacoustic apparatus according to a first exemplary embodiment and a second exemplary embodiment.

Since a restriction on a frequency band that can be received by an acoustic wave receiver exists, it is difficult to receive photoacoustic waves of all frequency components. For that reason, a frequency band to be measured is to be decided in the acoustic wave receiver. For example, in a case where a blood vessel having a certain size is set as an observation target, the frequency band of the acoustic wave receiver is decided in accordance with a frequency distribution of a photoacoustic wave generated in the blood vessel having the certain size. However, since a photoacoustic wave generated from an object also contains a frequency component different from a frequency component of the photoacoustic wave mainly generated by the blood vessel set as the observation target, if the frequency band is decided as described above, the frequency component where the measurement is difficult exists. For that reason, an accuracy of an initial acoustic pressure distribution is accordingly decreased by the frequency component that cannot be measured.

That is, an initial acoustic pressure distribution $\delta p_0$ may be different from the real initial acoustic pressure distribution $p_0$ in some cases. For that reason, an accuracy of an optical fluence distribution obtained by solving, for example, an optical diffusion equation illustrated in Expression (4) by using the initial acoustic pressure distribution $\delta p_0$ may be low in some cases.

For that reason, when an absorption coefficient distribution is obtained by dividing the initial acoustic pressure distribution $\delta p_0$ by the optical fluence distribution $\varphi$ and the Gruneisen coefficient distribution $\Gamma$ on the basis of Expression (2), an accuracy of the absorption coefficient distribution is also decreased.

In view of the above-described issues, the inventor of the present invention has conceived a technique of obtaining the optical fluence distribution $\varphi$ by adding an initial acoustic pressure distribution correction $p_{OB}$ to the initial acoustic pressure distribution $\delta p_0$ to be approximated to the real initial acoustic pressure distribution $p_0$. Furthermore, the inventor of the present invention has found a technique of obtaining the optical fluence distribution $\varphi$ while it is supposed that the initial acoustic pressure distribution correction $p_{OB}$ is attributable to the photoacoustic wave that cannot be measured by the acoustic wave receiver. That is, the inventor of the present invention has conceived a technique of obtaining the optical fluence distribution $\varphi$ that satisfies an expression representing an optical propagation including the initial acoustic pressure distribution $\delta p_0$ and the initial acoustic pressure distribution correction $p_{OB}$ derived from the photoacoustic wave that cannot be measured by the acoustic wave receiver.

For example, as illustrated in Expression (5), by solving an optical diffusion equation including the initial acoustic pressure distribution $\delta p_0$ and the initial acoustic pressure distribution correction $p_{OB}$, it is possible to obtain the highly accurate optical fluence distribution $\varphi$.

$$-\nabla \cdot \{D(\vec{r})\nabla\varphi(\vec{r})\} + \{\delta p_0(\vec{r}) + p_{OB}(\vec{r})\}/\Gamma(\vec{r}) = s(\vec{r}) \qquad (5)$$

As described above, a consideration will be given of a setting of $p_{OB}$ such that a sum of the initial acoustic pressure distribution $\delta p_0$ and the initial acoustic pressure distribution correction $p_{OB}$ included in Expression (5) is approximated to the real initial acoustic pressure distribution $p_0$. With this configuration, it is possible to obtain an effect close to an effect of the obtainment of the optical fluence distribution $\varphi$ by using the real initial acoustic pressure distribution as illustrated in Expression (3). That is, the optical fluence distribution $\varphi$ obtained by Expression (5) is approximated to a real value as compared with the optical fluence distribution obtained without taking the initial acoustic pressure distribution correction $p_{OB}$ into account such as, for example, the optical fluence distribution obtained by Expression (4).

Then, an absorption coefficient distribution $\mu_a$ obtained by dividing the sum of the initial acoustic pressure distribution $\delta p_0$ and the initial acoustic pressure distribution correction $p_{OB}$ by the optical fluence distribution $\varphi$ and the Gruneisen coefficient distribution $\Gamma$ on the basis of Expression (6) is approximated to the real value as compared with the case where the difference $p_{OB}$ is not taken into account. It is noted that Expression (6) is obtained by replacing the initial acoustic pressure distribution $p_0$ in Expression (2) by the sum of the initial acoustic pressure distribution $\delta p_0$ and the initial acoustic pressure distribution correction $p_{OB}$.

$$\delta p_0(\vec{r}) + p_{OB}(\vec{r}) = \Gamma(\vec{r})\mu_a(\vec{r})\varphi(\vec{r}) \qquad (6)$$

In addition, other object information obtained on the basis of the thus obtained absorption coefficient distribution $\mu_a$ is also approximated to the real value.

The object information obtained by the photoacoustic apparatus according to the present invention includes the absorption coefficient distribution of the object, a concentration distribution of a substance constituting the object, and the like. A concentration of the substance includes an oxygen saturation, an oxyhemoglobin concentration, a deoxyhemoglobin concentration, a total hemoglobin concentration, and the like. The total hemoglobin concentration is a sum of the oxyhemoglobin concentration and the deoxyhemoglobin concentration.

Hereinafter, an example in which the initial acoustic pressure distribution correction $p_{OB}$ is supposed to be derived from the photoacoustic wave that cannot be measured by the acoustic wave receiver will be described. It is however noted that according to the present invention, the initial acoustic pressure distribution correction may be generated from a derivation of any factor other than this. For example, the decrease in the accuracy caused when the initial acoustic pressure distribution is obtained from the received signal of the photoacoustic wave may be corrected.

In addition, hereafter, an example in which the present invention is applied to the optical diffusion equation will be described, but the expression representing the optical propagation to which the present invention can be applied is not limited to this. So long as the expression represents the optical propagation with which the optical fluence distribution can be obtained by using the real initial acoustic pressure distribution $p_0$, the present invention can be applied to the expression. For example, in this case, the present invention can be applied to the expression by replacing the real initial acoustic pressure distribution $p_0$ in the expression representing the optical propagation by the sum of the initial acoustic pressure distribution $\delta p_0$ and the initial acoustic pressure distribution correction $p_{OB}$.

First Exemplary Embodiment

According to a first exemplary embodiment, an example in which the optical fluence distribution is obtained by using the initial acoustic pressure distribution obtained by the photoacoustic apparatus according to the present exemplary embodiment and the initial acoustic pressure distribution correction derived from the photoacoustic wave that cannot be measured by the acoustic wave receiver will be described.

According to the present exemplary embodiment, it is considered that a corresponding absorption coefficient exists in the photoacoustic wave that cannot be measured by the acoustic wave receiver. This absorption coefficient is set as a background absorption coefficient distribution $\mu_{aB}$. That is, according to the present exemplary embodiment, the initial acoustic pressure distribution correction $p_{OB}$ can be written as Expression (7).

$$p_{OB}(\vec{r}) = \Gamma(\vec{r})\mu_{aB}(\vec{r})\phi(\vec{r}) \quad (7)$$

It is noted that the background absorption coefficient distribution $\mu_{aB}$ may be a uniform value irrespective of the position or different values at a plurality of positions in the object. For example, an average value of the absorption coefficients in the object can be set as the values of the background absorption coefficient distributions at the respective positions in the object. Otherwise, the object is divided into a plurality of regions, and average values of the absorption coefficients in the respective regions can also be set as the values of the background absorption coefficient distributions at the respective positions in the respective regions.

The photoacoustic apparatus according to the present exemplary embodiment will be described by using the schematic diagram illustrated in FIG. 1. The photoacoustic apparatus according to the present exemplary embodiment includes a light source 110, an optical system 120, a transducer array 130 as an acoustic wave reception unit, a computer 150 as a processing unit, a display apparatus 160, an input unit 170, and an absorption coefficient obtaining unit 180.

Hereinafter, the respective configurations of the photoacoustic apparatus according to the present exemplary embodiment will be described.

Object 100 and Optical Absorbent 101

Although an object 100 and an optical absorbent 101 do not constitute a part of the photoacoustic apparatus according to the present invention, the configurations will be described below. The photoacoustic apparatus according to the present invention mainly aims at performing a diagnosis of a malignant tumor, a blood vessel trouble, or the like of a human body or an animal, a follow-up observation of a chemical treatment, or the like. Therefore, a living matter, specifically, a target site for the diagnosis such as a breast, a neck region, or an abdominal region, of a human body or an animal is supposed as the object 100.

The optical absorbent 101 inside the object 100 is set as an observation target. The optical absorbent 101 is an optical absorbent having a relatively high absorption coefficient inside the object 100. In addition, it is supposed that the optical absorbent 101 is sufficiently smaller than the object 100. For example, in a case where the object 100 is a human body, a blood vessel or a new blood vessel containing oxyhemoglobin, deoxyhemoglobin, methemoglobin, or those is an objective of the optical absorbent 101. In addition to the above, a plaque of a carotid wall or the like also is also the objective. In addition, in a case where a contrast agent is used, the contrast agent becomes the objective of the optical absorbent 101.

Light Source 110

The light source may be a pulse light source that can generate pulsed light on the order of several nano to several micro seconds in order that the photoacoustic wave is efficiently generated. Specifically, the light source generates light having a pulse width higher than or equal to 5 nsec and lower than or equal to 500 nsec.

In addition, a wavelength of the light may be a wavelength at which the light propagates into the object. Specifically, in a case where the object is the living matter, to avoid the optical absorption by water, the light source generates light having a wavelength approximately higher than or equal to 400 nm and approximately lower than or equal to 1600 nm. Moreover, to measure the optical absorbent having a wavelength dependency, the light source may be a light source that can generate different wavelengths instead of a light source that generates only light having a single wavelength.

For example, a laser, a light emitting diode, or the like can also be used as the light source. Various lasers such as a solid-state laser, a gas laser, a dye laser, a semiconductor laser, or a laser using optical parametric oscillators (OPO) can be used as the laser.

Optical System 120

The optical system 120 is a member that processes the light emitted from the light source into a desired light distribution shape to be guided to the object 100. The optical system 120 is constituted by optical parts such as a lens and a mirror, an optical waveguide such as optical fiber, and the like. For example, the optical parts include a mirror that reflects the light, a lens that focuses or expands the light or changes the shape, a diffusing plate that diffuses the light, and the like. Any configuration of the optical system 120 described above may be used so long as the object is irradiated with the light emitted from the light source with a desired shape. In addition, the intensity may be selected such that a ratio of the signal to the noise can be secured while a safety of the living matter is ensured.

In a case where the entire region cannot be irradiated at a desired intensity at once since the region where the object information of the object is desired to obtained is wide, a configuration may be adopted such that the desired region can be irradiated at a sufficient intensity by performing the irradiation plural times to carry out scanning, for example.

Transducer Array 130

Any transducer may be used as an acoustic wave receiver used in a transducer array 130 so long as the transducer can receive an acoustic wave and convert the acoustic wave into an electric signal. A reception band of the transducer is designed in accordance with a size of the observation target such that the frequency component of the photoacoustic wave generated from the observation target by the transducer array 130 can be received as much as possible.

For example, a transducer using a piezoelectric phenomenon, an optical resonance, a change in an electrostatic capacitance, or the like can be used as the transducer.

To obtain a spatial distribution of the object information without using advance information such as a shape of the object, the acoustic waves are to be received at a plurality of positions. In view of the above, as in the present exemplary embodiment, the transducers may be arranged in an array, and the acoustic wave may be received at the plurality of positions at the same time. In addition, while a moving unit moves the transducer, the transducer may receive the acoustic waves at the plurality of positions.

Acoustic Matching Material 140

Although an acoustic matching material 140 does not constitute a part of the photoacoustic apparatus according to the present invention, the acoustic matching material 140 will be described below. The acoustic matching material 140 is a member configured to realize acoustic matching between the object 100 and the transducer array 130 by being arranged between the object 100 and the transducer array 130. Water, gel composed of water, oil, alcohol, and the like, etc. can be used as the acoustic matching material 140.

Computer 150

A workstation, a large-scale parallel clusters, or the like is typically used as the computer 150, and correction processing, image reconstruction processing, or the like is performed by previously-programmed software. It is noted that the object information can also be obtained by hardware processing instead of software processing performed in the workstation. In addition, the respective processings executed by the computer 150 according to the present exemplary embodiment may be performed by mutually different apparatuses.

An arithmetic operation unit 152 in the computer 150 can apply predetermined processing to the electric signal output from the transducer array 130.

Figure 2:
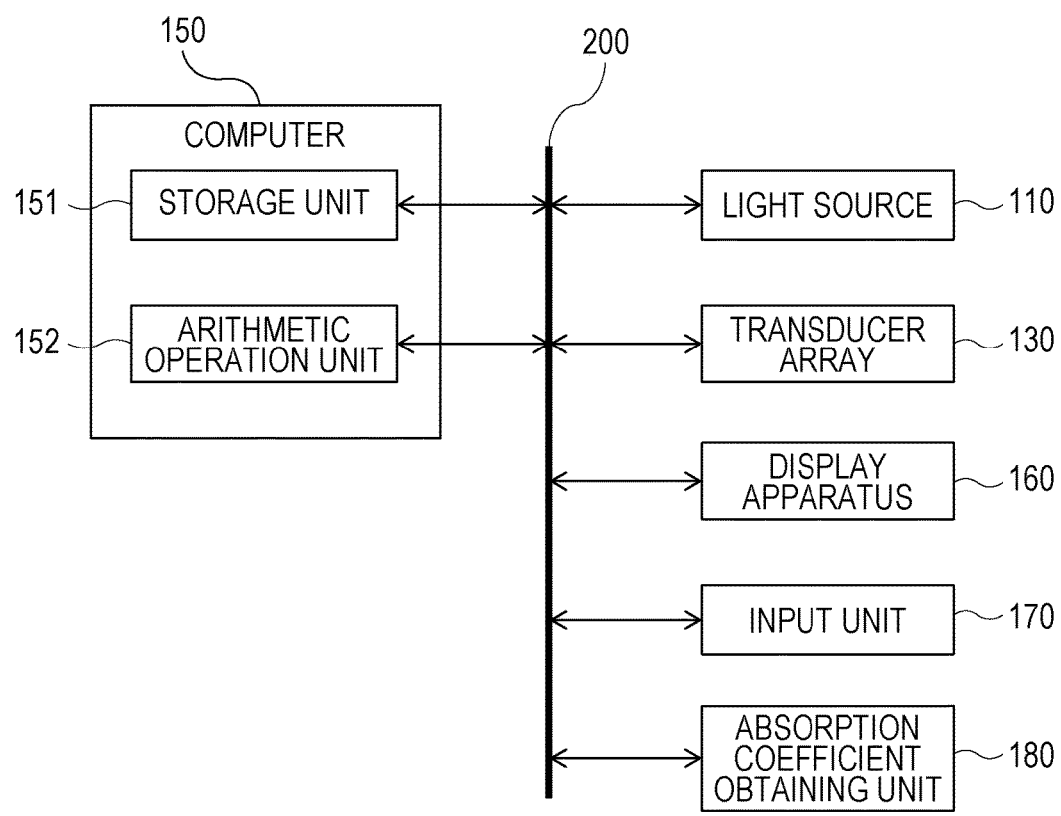
FIG. 2 illustrates a connection between a computer and the other configurations.

In addition, the arithmetic operation unit 152 functioning as a controlling unit can control operations of the respective configurations constituting the photoacoustic apparatus via a bus 200 as illustrated in FIG. 2. For example, the arithmetic operation unit 152 controls a light emission timing of the light generated from the light source and can control a reception timing of the photoacoustic wave while the light is used as a trigger signal.

The arithmetic operation unit 152 is typically constituted by an element such as a CPU, a GPU, or an analog-to-digital converter or a circuit such as an FPGA or an ASIC. It is noted that the arithmetic operation unit 152 may be constituted by a plurality of elements or circuits instead of being constituted by a single element or circuit. In addition, the respective processings performed by the arithmetic operation unit 152 may be executed by any of the elements or circuits.

A storage unit 151 in the computer 150 is typically constituted by a storage medium such as a ROM, a RAM, and a hard disc. It is noted that the storage unit 151 may be constituted by a plurality of storage media instead of being constituted by a single storage medium.

Moreover, the computer 150 is configured such that pipeline processing of a plurality of signals can be performed at the same time. Accordingly, it is possible to shorten the time to obtain the object information.

Programs for executing the signal processing performed by the computer 150 and the operation control of the photoacoustic apparatus can be saved in the storage unit 151. It is noted that the storage unit 151 in which the programs are saved is a non-transient recording medium.

Display Apparatus 160

The display apparatus 160 is an apparatus configured to display an image of the object information output from the computer 150, numeric information, and the like. A display of any system such as a liquid crystal display, a plasma display, an organic EL display, and an FED can be adopted as the display apparatus 160. The display apparatus 160 may be provided separately from the photoacoustic apparatus according to the present invention.

Input Unit 170

The input unit 170 is a member configured to enable a user to specify information for inputting the information to the computer 150. A key board, a mouse, a touch panel, a dial, a button, and the like can be used as the input unit 170. In a case where the touch panel is adopted as the input unit 170, the display apparatus 160 may be a touch panel also functioning as the input unit 170.

Absorption Coefficient Obtaining Unit 180

The absorption coefficient obtaining unit 180 is an apparatus configured to obtain the background absorption coefficient distribution of the object 100. For example, a time-resolved spectroscopy system configured to introduce time-resolved spectroscopy to near-infrared spectroscopy and obtain the background absorption coefficient distribution of the object 100 can be adopted as the absorption coefficient obtaining unit 180. In addition to the above, various image forming apparatuses such as an MRI, a CT, and an ultrasonic diagnostic apparatus can be adopted as the absorption coefficient obtaining unit 180. The background absorption coefficient distribution obtained at this time may be a spatially uniform value (for example, an average value in the object 100) or may have a spatial distribution.

In a case where the time-resolved spectroscopy system or the like is adopted as the absorption coefficient obtaining unit 180, the absorption coefficient obtaining unit 180 may obtain a reduced scattering coefficient distribution $\mu_s'$ or the diffusion coefficient distribution D as well. The reduced scattering coefficient distribution or the diffusion coefficient distribution obtained at this time may be a spatially uniform value (for example, an average value in the object 100) or may have a spatial distribution. It is noted that a reduced scattering coefficient distribution $\mu_s'$ and the diffusion coefficient distribution D are coefficients defined by Expression (8) and Expression (9). Where g denotes a scattering anisotropy, and $\mu_s$ denotes a scattering coefficient.

$$\mu_s' := (1-g)\mu_s \qquad (8)$$

$$D(\vec{r}) = \{3(\mu_{aB}(\vec{r}) + \mu_s'(\vec{r}))\}^{-1} \qquad (9)$$

The arithmetic operation unit 152 may estimate the values of the background absorption coefficient distributions in the respective regions on the basis of the image of the inside of the object 100 obtained by the image forming apparatus functioning as the absorption coefficient obtaining unit 180.

In this case, the arithmetic operation unit 152 can be configured as a part of the absorption coefficient obtaining unit 180.

Next, an operation of the photoacoustic apparatus according to the present exemplary embodiment will be described by using a flow illustrated in FIG. 3.

S100: Step of obtaining the received signal of the photoacoustic wave

First, the light source 110 generates light 121, and the object 100 is irradiated with the light 121 via the optical system 120. Then, the light 121 is absorbed by the optical absorbent 101 located inside the object 100. When the optical absorbent 101 that has absorbed the light 121 instantaneously expands, the photoacoustic wave 102 is generated.

The transducer array 130 receives the photoacoustic waves 102 and converts the photoacoustic waves 102 into time-series received signals. The computer 150 amplifies the time-series received signals output from the transducer array 130 and performs AD conversion of the time-series received signals to be stored in the storage unit 151 inside the computer 150. According to the present exemplary embodiment, the computer 150 starts the above-described processing with respect to the received signal output from the transducer array 130 at a timing when the light source 110 generates the light 121.

It is noted that the intensity information of the light 121 with which the object 100 is irradiated in the present step is stored in the storage unit 151 and used for a boundary condition of the irradiation light which will be described in S400 below.

S200: Step of obtaining the initial acoustic pressure distribution by using the received signal of the photoacoustic wave The computer 150 performs the reconstruction processing as described in Non-patent document 1 by using the time-series received signals stored in the storage unit 151 and can form the initial acoustic pressure distribution $\delta p_0$ in the object 100. Back projection in a time domain or Fourier domain normally used in a tomography technology, delay & sum (D & S), or the like is used as a reconstruction algorithm. In addition, in a case where much time can be used for the reconstruction, an image reconstruction technique such as an iteration method used in the fields such as inverse problem can also be used.

In a case where the transducer focused in S100 is sequentially moved to obtain the time-series received signals, a high-dimensional initial acoustic pressure distribution can be formed without the reconstruction. In this case, the computer 150 does not need to perform the reconstruction processing.

S300: Step of obtaining the background absorption coefficient distribution of the object According to the present exemplary embodiment, the time-resolved spectroscopy system functioning as the absorption coefficient obtaining unit 180 obtains the background absorption coefficient distribution. In addition, according to the present exemplary embodiment, the absorption coefficient obtaining unit 180 also obtains the reduced scattering coefficient distribution. The background absorption coefficient distribution or the reduced scattering coefficient distribution obtained at this time may be a spatially uniform value (for example, an average value in the object 100) or may have a spatial distribution.

It is noted that the user may select the background absorption coefficient distribution in the present step. For example, the user may select the desired background absorption coefficient distribution from among the plurality of background absorption coefficient distributions stored in the storage unit 151 by using the input unit 170.

In a case where the object 100 is a living matter, first, the user may input information such as an age and a gender of the object 100 by using the input unit 170, and the input information may be output to the computer 150. Subsequently, the arithmetic operation unit 152 can select a statistic score of the background absorption coefficient distribution corresponding to the information input by the user from among statistic scores of the plurality of background absorption coefficient distributions stored in the storage unit 151.

The user may also check an image of the inside of the object 100 obtained by the image forming apparatus and input the values of the background absorption coefficient distributions in the respective regions by using the input unit 170.

The user can also similarly input the diffusion coefficient distribution or the reduced scattering coefficient distribution by using the input unit 170.

In a case where a previously set value is used as the background absorption coefficient distribution of the object 100 in S400 which will be described below, the present step does not need to be performed.

S400: Step of obtaining the optical fluence distribution by using an equation representing the optical propagation including the initial acoustic pressure distribution and the correction term including the background absorption coefficient distribution The arithmetic operation unit 152 obtains the optical fluence distribution in the object 100 by using the expression representing the optical propagation including the initial acoustic pressure distribution obtained in S200 and the correction term including the background absorption coefficient distribution of the object 100 obtained in S300. This expression representing the optical propagation will be described below in detail.

Figure 4A:
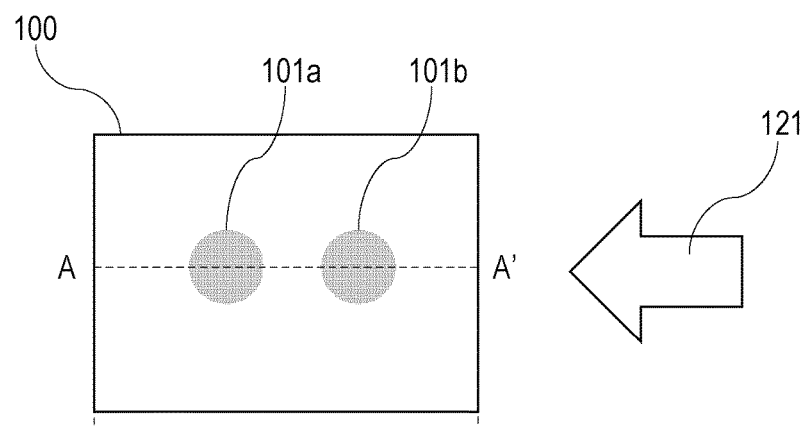
FIG. 4A illustrates a situation where light irradiation is performed according to the first exemplary embodiment.
Figure 4B:
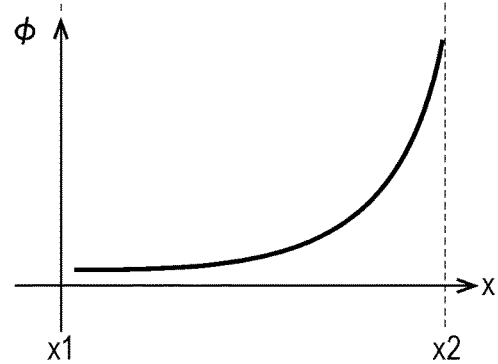
FIG. 4B schematically illustrates an optical fluence distribution in an object.

FIG. 4A illustrates the irradiation state of the light 121 according to the present exemplary embodiment. Herein, a case will be considered in which the object 100 is irradiated with the light 121, and intense optical absorption occurs in optical absorbents 101a and 101b. FIG. 4B schematically illustrates the optical fluence distribution on A-A' in the object 100 when the object 100 is irradiated with the light 121.

Figure 5A:
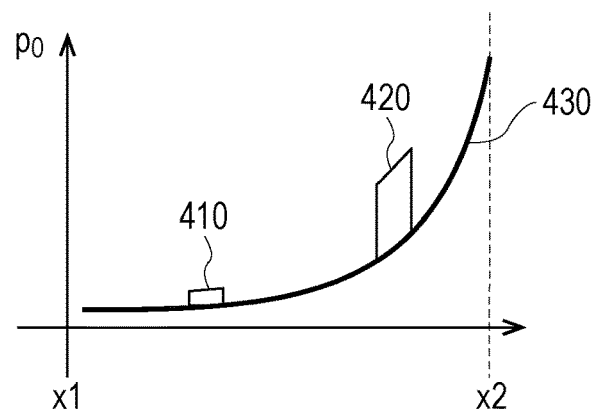
FIG. 5A schematically illustrates a real initial acoustic pressure distribution of a photoacoustic wave according to the first exemplary embodiment.

FIG. 5A schematically illustrates the real initial acoustic pressure distribution $p_0$ of the photoacoustic wave generated on A-A' in the case illustrated in FIG. 4A. That is, real initial acoustic pressure distributions 410 and 420 corresponding to the photoacoustic waves are generated on the optical absorbents 101a and 101b. Similarly, an initial acoustic pressure 430 corresponding to the photoacoustic wave having a low frequency component generated over the entire object 100 is also the real initial acoustic pressure distribution.

However, since the transducer array 130 normally has a restriction on the frequency band, it is difficult to measure all the frequency components of the generated photoacoustic wave. The transducer 130 according to the present exemplary embodiment is configured to mainly receive the frequency components of the photoacoustic waves generated on the optical absorbents 101a and 101b. For that reason, the initial acoustic pressure distribution $\delta p_0$ obtained by using the received signal from the transducer 130 takes a shape schematically illustrated in FIG. 5B, and it is hard to mention that the initial acoustic pressure 430 is reproduced.

Figure 5B:
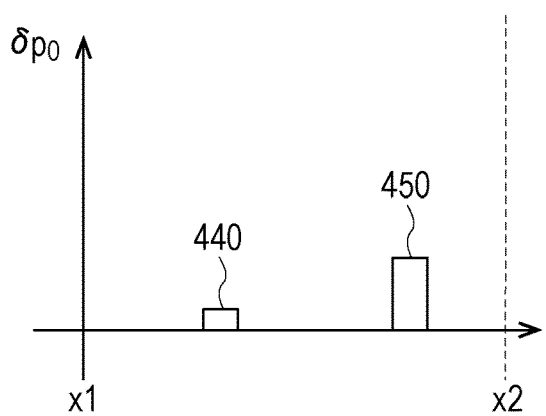
FIG. 5B schematically illustrates an initial acoustic pressure distribution obtained from a received signal according to the first exemplary embodiment.
Figure 5C:
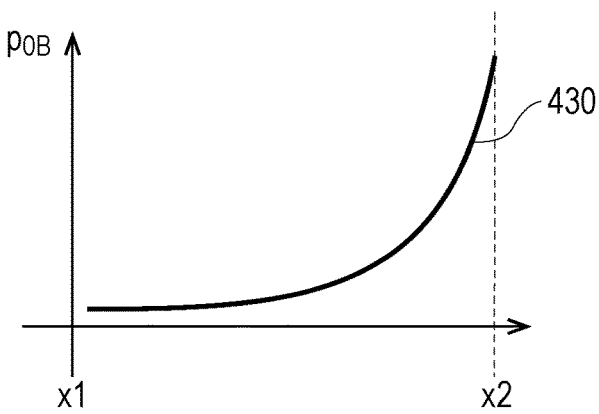
FIG. 5C schematically illustrates a difference between a true value of the initial acoustic pressure distribution and an actual measurement value according to the first exemplary embodiment.

As may be understood from the comparison between FIG. 5A and FIG. 5B, the real initial acoustic pressure distribution $p_0$ is different from the initial acoustic pressure distribution $\delta p_0$. Herein, a difference between the real initial acoustic pressure distribution $p_0$ and the initial acoustic pressure distribution $\delta p_0$ is illustrated in FIG. 5C. If it is possible to perform a setting such that the initial acoustic pressure distribution correction $p_{OB}$ is the same as the difference illustrated in FIG. 5C, a sum of the initial acoustic pressure distribution $\delta p_0$ and the initial acoustic pressure distribution correction $p_{OB}$ is supposed to be the real initial acoustic pressure distribution $p_0$.

As described above, according to the present exemplary embodiment, the initial acoustic pressure distribution correction $p_{OB}$ is represented by Expression (7). That is, the inventor of the present invention has considered that the difference between the real initial acoustic pressure distribution $p_0$ and the initial acoustic pressure distribution $\delta p_0$ illustrated in FIG. 5C is derived from the background absorption coefficient distribution $\mu_{aB}$.

When the optical diffusion equation illustrated in Expression (5) is assigned to Expression (7), Expression (10) can be obtained.

$$-\nabla \cdot \{D(\vec{r})\nabla\phi(\vec{r})\} + \{\delta p_0(\vec{r}) + \Gamma(\vec{r})\mu_{aB}(\vec{r})\phi(\vec{r})\}/\Gamma(\vec{r}) = s(\vec{r}) \quad (10)$$

Herein, $\Gamma\mu_{aB}\phi$ in Expression (10) is equivalent to the "correction term including the background absorption coefficient distribution" according to the present exemplary embodiment. The initial acoustic pressure distribution $\delta p_0$ is obtained in S200, and the background absorption coefficient distribution $\mu_B$ and the diffusion coefficient distribution D are obtained in S300 according to the present exemplary embodiment. In addition, a certain value is set for the Gruneisen coefficient distribution $\Gamma$ by supposing the object. For example, 0.25 or the like is set by supposing the blood vessel. If the spatial distribution can be previously obtained, the value may be set for the Gruneisen coefficient distribution $\Gamma$. The user may input the Gruneisen coefficient distribution $\Gamma$ by using the input unit 170. Since only the optical fluence distribution $\phi$ in Expression (10) is a variable, the arithmetic operation unit 152 can obtain the optical fluence distribution $\phi$ by solving Expression (10).

Since the thus obtained optical fluence distribution is supposed to be approximated to the real value, because it is corrected by the contribution of the background absorption coefficient distribution which is not included in the initial acoustic pressure distribution. That is, it is possible to obtain the optical fluence distribution at a satisfactory accuracy by also using the background absorption coefficient distribution in addition to the initial acoustic pressure distribution. It is noted that even when an expression obtained by transforming Expression (10) is used, if the transformation is an equivalent transformation, a mode of obtaining the optical fluence distribution so as to satisfy the expression after the transformation is also included in the present invention.

S500: Step of obtaining the object information by using the initial acoustic pressure distribution and the optical fluence distribution The arithmetic operation unit 152 obtains the absorption coefficient distribution $\mu_a$ in the object 100 as the object information by Expression (6) and Expression (7). In the present step, since the absorption coefficient distribution $\mu_a$ is obtained by using the highly accurate optical fluence distribution $\phi$ obtained in S400, it is possible to obtain the highly accurate absorption coefficient distribution $\mu_a$.

Then, the arithmetic operation unit 152 can display the image of the thus obtained absorption coefficient distribution, the numeric information, and the like on the display apparatus 160.

As described above, according to the present exemplary embodiment, even in a case where the photoacoustic wave that cannot be measured by the acoustic wave receiver exists, by obtaining the optical fluence distribution by also using the background absorption coefficient distribution in addition to the initial acoustic pressure distribution, it is possible to obtain the optical fluence distribution in the object at a satisfactory accuracy.

It is noted that the steps from S100 to S500 may be executed by using light having different wavelengths, and the absorption coefficient distributions corresponding to the lights having the different wavelengths may be obtained. In addition, the arithmetic operation unit 152 may obtain a concentration distribution of the substance constituting the object 100 as the object information by using the plurality of absorption coefficient distributions respectively corresponding to the plurality of wavelengths. According to the present exemplary embodiment, since each of the absorption coefficient distributions corresponding to the lights at the respective wavelengths is obtained at a satisfactory accuracy, it is also possible to obtain the concentration distribution of the substance which is obtained by using these distributions at a satisfactory accuracy.

Second Exemplary Embodiment

According to the method of the first exemplary embodiment, in a case where the accuracy of the background absorption coefficient distribution to be used is not sufficient, the highly accurate optical fluence distribution cannot be obtained, and the absorption coefficient distribution cannot also be obtained at a high accuracy. In view of the above, according to the second exemplary embodiment, the object is irradiated with the light in each of a plurality of irradiation states different from each other. Then, the background absorption coefficient distribution is obtained by solving an optimization situation in which an objective function including a relational expression based on the plurality of initial acoustic pressure distributions corresponding to the plurality of irradiation states, the plurality of optical fluence distributions corresponding to the plurality of irradiation states, the absorption coefficient distribution of the optical absorbent in the object, and the Gruneisen coefficient distribution in the object is minimized.

The absorption coefficient distribution of the optical absorbent mentioned herein refers to $\delta\mu_a$ illustrated in Expression (11) and means the absorption coefficient corresponding to the photoacoustic wave that can be measured by the acoustic wave receiver. As may be understood from the definition or the calculation to subtract sides of Expression (7) from Expression (6), the absorption coefficient distribution $\delta\mu_a$ of the optical absorbent is obtained by subtracting the background absorption coefficient distribution $\mu_{aB}$ from the absorption coefficient distribution $\mu_a$.

$$\delta p_0(\vec{r}) = \Gamma(\vec{r})\delta\mu_a(\vec{r})\phi(\vec{r}) \quad (11)$$

According to the present exemplary embodiment, even in a case where the accuracy of the background absorption coefficient distribution is not sufficient or a case where the background absorption coefficient distribution cannot be obtained, it is possible to obtain the background absorption coefficient distribution at a satisfactory accuracy.

In addition, according to the present exemplary embodiment, even in a case where the photoacoustic wave that cannot be measured by the acoustic wave receiver exists, it is possible to obtain the absorption coefficient distribution at a satisfactory accuracy.

It is noted that the different irradiation states mentioned in the present specification refer to a situation where the light irradiation positions with respect to the object are varied. The measurement is performed by changing the light irradiation positions to an extent that the initial acoustic pressure distributions between the irradiation states are significantly different from each other.

With regard to a parameter other than the background absorption coefficient distribution used for obtaining the optical fluence distribution too, similarly as in the background absorption coefficient distribution, the parameter can be obtained at a satisfactory accuracy by iteration arithmetic operation. It is noted that according to the present exemplary embodiment, an example in which values of the diffusion coefficient distribution and the absorption coefficient distribution of the optical absorbent in addition to the background absorption coefficient distribution are also obtained by solving the optimization issue will be described.

A configuration of the photoacoustic apparatus according to the present exemplary embodiment is the same as the configuration illustrated in the first exemplary embodiment. As described above, the optical system 120 and the transducer array 130 are to be operated such that initial acoustic pressure distributions in different irradiation states can be obtained.

Figure 6:
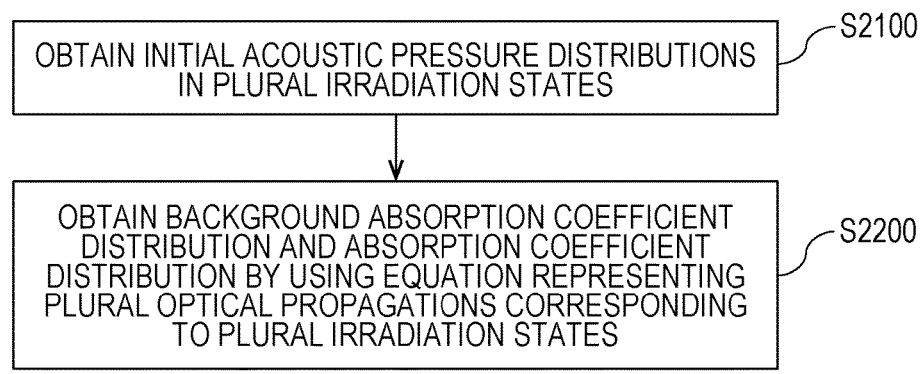
FIG. 6 illustrates an operation flow of the second exemplary embodiment.

Hereinafter, an operation of the photoacoustic apparatus according to the present exemplary embodiment will be described by using a flow illustrated in FIG. 6. It is noted that according to the present exemplary embodiment too, the computer 150 controls the operations of the respective configurations constituting the photoacoustic apparatus illustrated in FIG. 1.

S2100: Step of obtaining the initial acoustic pressure distributions in a plurality of irradiation states First, steps S100 and S200 according to the first exemplary embodiment are performed in a first irradiation state to obtain a first initial acoustic pressure distribution $\delta p_0^{(1)}$.

Subsequently, steps in S100 and S200 are performed by changing the irradiation state into a second irradiation state to obtain a second initial acoustic pressure distribution $\delta p_0^{(2)}$. According to the present exemplary embodiment, for simplicity of the descriptions, the example of the irradiation states of the lights in the two patterns has been illustrated, but irradiation states of the lights in three or more patterns may also be used.

S2200: Step of obtaining the background absorption coefficient distribution and the absorption coefficient distribution by using equation representing a plurality of optical propagations corresponding to the plurality of irradiation states The arithmetic operation unit 152 subsequently obtains the background absorption coefficient distribution and the absorption coefficient distribution by using an expression representing a plurality of optical propagations corresponding to the plurality of irradiation states which includes the initial acoustic pressure distributions obtained in S2100 and the correction term including the background absorption coefficient distribution of the object 100.

According to the present exemplary embodiment, Expression (12) is used as the expression representing the above-described optical propagations. Expression (12) is obtained by only rewriting Expression (10) for each the irradiation state of the light. In addition, the optimization issue for obtaining the background absorption coefficient distribution $\mu_{aB}$ and the absorption coefficient distribution $\delta\mu_a$ of the optical absorbent is solved such that an objective function including a relational expression f illustrated in Expression (13) and Expression (14) is minimized while satisfaction of an optical diffusion equation illustrated in Expression (12) is set as a constraint. The absorption coefficient distribution $\mu_a$ is obtained by adding the background absorption coefficient distribution $\mu_{aB}$ to the absorption coefficient distribution $\delta\mu_a$ of the optical absorbent which are obtained as a result of the solution of the above-described optimization issue.

That is, the arithmetic operation unit 152 obtains the background absorption coefficient distribution $\mu_{aB}$ and the absorption coefficient distribution $\delta\mu_a$ of the optical absorbent such that the objective function including the relational expression f illustrated in Expression (13) and Expression (14) based on the optical fluence distribution $\varphi^{(i)}$ in each of the respective irradiation states, the absorption coefficient distribution $\delta\mu_a$ of the optical absorbent, the Gruneisen coefficient distribution $\Gamma$ in the object, and the initial acoustic pressure distribution $\delta p_0^{(i)}$ in each of the respective irradiation states is minimized while the satisfaction of the expression illustrated in Expression (12) representing the optical propagation including the initial acoustic pressure distribution $\delta p_0^{(i)}$ and the correction term including the background absorption coefficient distribution $\mu_{aB}$ is set as the constraint.

$$-\nabla \cdot \{D(\vec{r})\nabla \phi^{(i)}(\vec{r})\} + \mu_{aB}(\vec{r})\phi^{(i)}(\vec{r}) + \delta p^{(i)}(\vec{r})/\Gamma(\vec{r}) = s(\vec{r}) \qquad (12)$$

$$f = \sum_i \int \frac{1}{2} h^{(i)}(\vec{r})^2 d\vec{r} \qquad (13)$$

$$h^{(i)}(\vec{r}) = \Gamma(\vec{r})\delta\mu_a(\vec{r})\phi^{(i)}(\vec{r}) - \delta p^{(i)}(\vec{r}) \qquad (14)$$

In a case where the above-described optimization issue is solved by a numeric calculation, since it is extremely difficult to strictly reach the minimum value of the objective function, the calculation may be terminated in accordance with an accuracy. In this case too, in common practices, it can be mentioned that the calculation has been carried out until the objective function has been minimized.

Expression (12) is merely one aspect of the expression representing the optical propagation including the initial acoustic pressure distribution $\delta p_0^{(i)}$ and the correction term including the background absorption coefficient distribution $\mu_{aB}$. In addition, Expression (13) and Expression (14) are merely one aspect of the relational expression of the optical fluence distribution $\varphi^{(i)}$ in each of the respective irradiation states, the absorption coefficient distribution of the optical absorbent, the Gruneisen coefficient distribution $\Gamma$ in the object, and the initial acoustic pressure distribution $\delta p_0^{(i)}$ in each of the respective irradiation states. Therefore, an expression representing a different optical propagation or a different relational expression may be adopted.

The arithmetic operation unit 152 can also obtain the other object information on the basis of the absorption coefficient distribution $\mu_a$.

According to the method of the present exemplary embodiment described above, even in a case where the sufficiently accurate background absorption coefficient distribution cannot be obtained, it is possible to obtain the background absorption coefficient distribution at a satisfactory accuracy. In addition, since the optical fluence distribution is obtained by using the initial acoustic pressure distribution and the background absorption coefficient distribution, even in a case where the decrease in the value of the initial acoustic pressure derived from the background absorption coefficient distribution occurs, it is possible to obtain the absorption coefficient distribution of the object at a satisfactory accuracy.

Example 1

According to the present example, an example in which a numeric experiment based on the first exemplary embodiment is performed will be described.

The object 100 has a cubic shape of 5 cm×5 cm×5 cm. The light 121 having the wavelength of 700 nm is incident on an entire surface of an upper part of the object 100. It is noted that the intensity of the light 121 is set as 10 mJ/m$^2$, and a value of the Gruneisen coefficient distribution is set as 1.

The optical absorbent 101 has a torus shape to imitate a blood vessel, where a major radius is set as 1.5 cm, and a minor radius is set as 1 mm. The optical absorbent 101 is arranged such that a center of the torus optical absorbent 101 is matched with a center of the cubic object 100. In addition, the optical absorbent 101 is arranged such that a central axis of the torus ring is orthogonal to a certain side face of the cubic object 100. It is supposed that the optical absorbent 101 is hemoglobin, and the density is to an extent that the hemoglobin normally exists in the blood vessel of the human body. The oxygen saturation is supposed to be 90%. For that reason, the absorption coefficient of the optical absorbent 101 with respect to the light having the wavelength of 700 nm is approximately 0.24 mm$^{-1}$. An absorption coefficient of a uniform value is set as the background absorption coefficient distribution irrespective of the position and is 0.0024 mm$^{-1}$ corresponding to a size that is 1% of the absorption coefficient of the optical absorbent 101. In addition, the reduced scattering coefficient is uniformly set as 0.96 mm$^{-1}$ irrespective of the position. The diffusion coefficient distribution is obtained from Expression (9).

Figure 7:
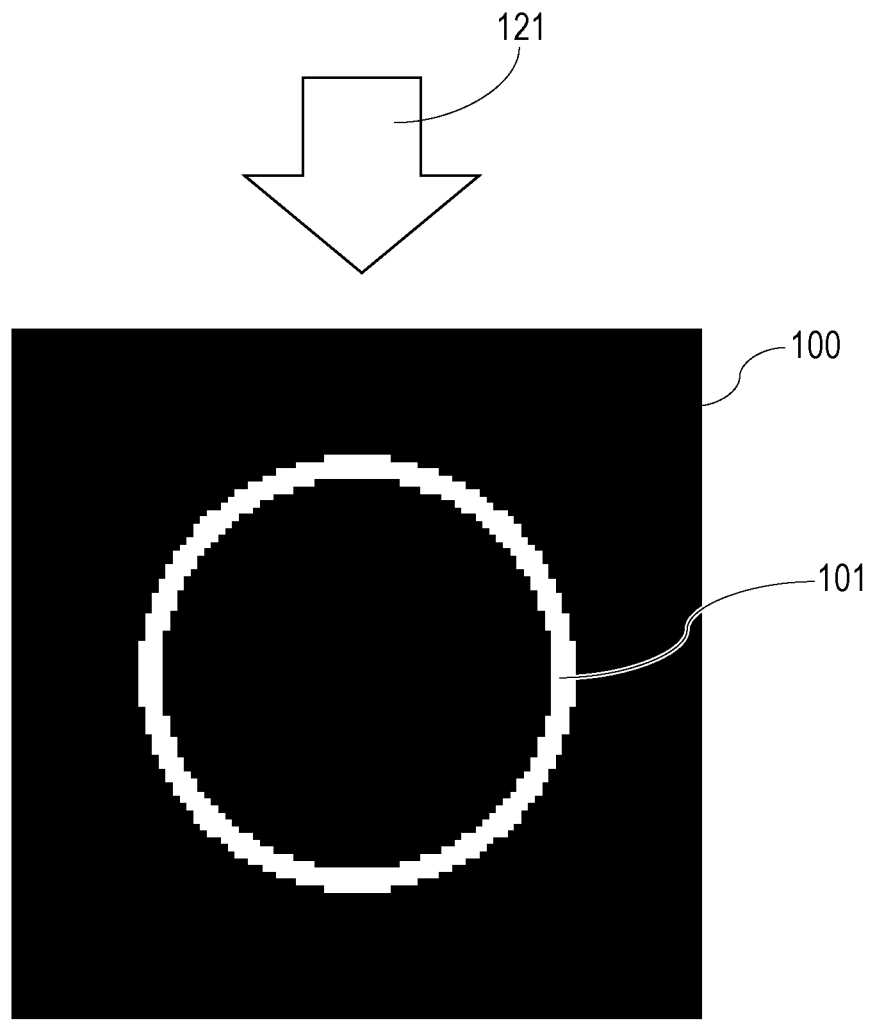
FIG. 7 illustrates a model used for a numeric experiment according to Example 1.

FIG. 7 illustrates a situation of the spatial distribution of the absorption coefficient in a certain cross section as vertically cut through the center of the object. It is noted that the unit of the absorption coefficient in FIG. 7, FIG. 10, and FIG. 11 is m$^{-1}$. Brightness in FIG. 7 represents a magnitude of the absorption coefficient. A white annular ring of FIG. 7 is the optical absorbent 101 having a relatively high absorption coefficient. A black part of FIG. 7 is a background structure of the optical absorbent 101 having a relatively low absorption coefficient, and the photoacoustic wave having a low frequency component which is difficult for the acoustic wave receiver to receive is generated. The light 121 is incident from an upper part on the paper plane.

The discretization is performed for the numeric calculation. The object 100 is subjected to the discretization by orthogonal equal-interval lattices, and the number of lattices of the respective axes is set as 100.

Figure 8:
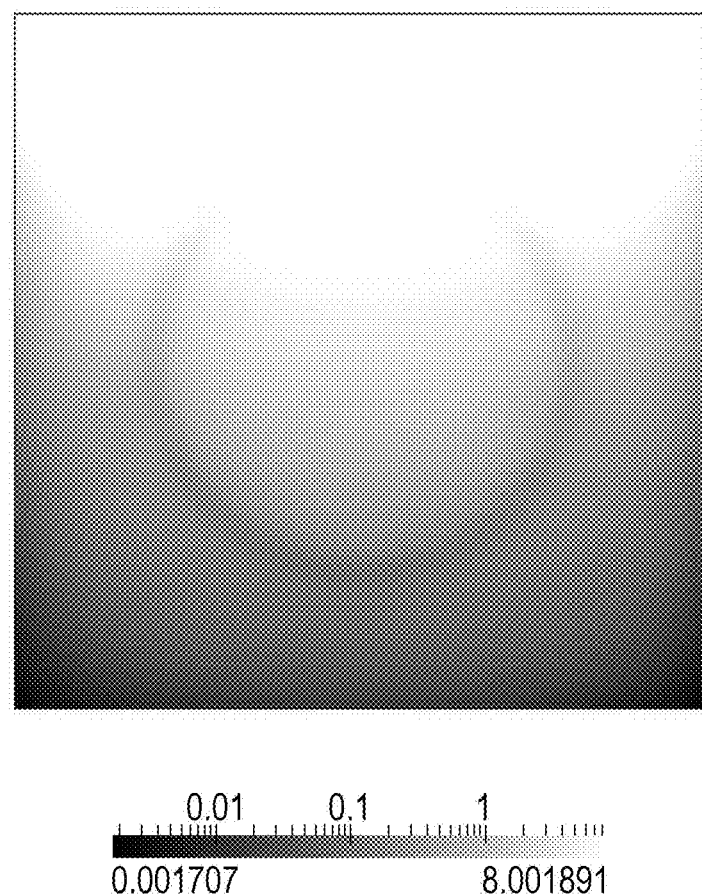
FIG. 8 illustrates an optical fluence distribution obtained when a simulated calculation of an observation result is performed according to Example 1.

A simulated calculation is also performed for an observation result since it is a numeric experiment this time. This calculation method also has an arbitrary property, but according to the present example, the following method is employed. First, with regard to the optical propagation, the spatial distribution of the optical fluence is obtained by using Expression (1). For a boundary condition of the optical fluence, a method proposed in D. Contini, et. al, "Photon migration through a turbid slab described by a model based on diffusion approximation". I. Theory", Appl. Phys. 36 (1997) 4587, which will be referred to as Non-patent document 2, is employed. The incidence of the light is represented by a method of setting a value in a source term of a boundary condition on the entire surface of the upper part of the object, and a refractive index of the object is set as 1.4. A central difference is used for the discretization method of Expression (1), and a conjugated gradient method is employed for a simultaneous linear equation to be solved until a square norm of residuals becomes lower than or equal to 10$^{-7}$. FIG. 8 illustrates a situation of the obtained spatial distribution of the optical fluence. A situation may be observed where the light incident from the upper part is transmitted to a lower part while being diffused and absorbed.

Next, step S100 of obtaining the received signal of the photoacoustic wave is executed. That is, the real initial acoustic pressure distribution $p_0$ can be obtained by Expression (2), and this propagates to the observation apparatus to be observed. However, As described already, the frequency band that can be measured by the observation apparatus has the restriction, and only a part thereof is measured. According to the present example, to reproduce it, the initial acoustic pressure distribution derived from the photoacoustic wave that cannot be measured by the acoustic wave receiver is set as a right side of Expression (7), that is, a product of the Gruneisen coefficient distribution, the background absorption coefficient distribution, and the optical fluence. Then, with regard to the signal observed in step S100, the photoacoustic wave equivalent to a difference between $p_0$ and the initial acoustic pressure distribution derived from the photoacoustic wave that cannot be measured by the acoustic wave receiver propagates to be observed as the signal.

Next, step S200 of obtaining the initial acoustic pressure distribution by using the received signal of the photoacoustic wave is executed. The initial acoustic pressure distribution $\delta p_0$ in the object 100 can be obtained by performing the reconstruction processing as described in Non-patent document 1. According to the present example, it is supposed that the reconstruction is ideally performed, and the difference between $p_0$ and the initial acoustic pressure distribution derived from the photoacoustic wave that cannot be measured by the acoustic wave receiver used in S100 is obtained as the initial acoustic pressure distribution $\delta p_0$.

Next, step S300 of obtaining the background absorption coefficient distribution of the object is executed. Herein, it is supposed that the time-resolved spectroscopy system where time-resolved spectroscopy is introduced to near-infrared spectroscopy ideally operates, and the background absorption coefficient distribution $\mu_{aB}$ and the reduced scattering coefficient distribution $\mu_s'$ which are uniform values irrespective of the position are correctly obtained. In addition, the diffusion coefficient distribution D that is a uniform value irrespective of the position is obtained on the basis of those values.

Next, step S400 of obtaining the optical fluence distribution by using the initial acoustic pressure distribution and the background absorption coefficient distribution is executed. The equation illustrated in Expression (10) may be solved with respect to φ. For the boundary condition of the optical fluence, the method proposed in Non-patent document 2 is used. The incidence of the light is represented by a method of setting a value in the source term of the boundary condition on the entire surface of the upper part of the object, and the refractive index of the object is set as 1.4. The central difference is used for the discretization method of Expression (10), and the conjugated gradient method is used for the simultaneous linear equation to be solved until the square norm of the residuals becomes lower than or equal to 10$^{-7}$.

It is noted that the discretization method and the solution method for the simultaneous linear equation used when Expression (10) is solved have an arbitrary property, and any method in the related art can be used for the solution. That is, the method according to the present example is merely an example. In addition, the user can appropriately set a threshold at which the calculation of the residuals used for solving the simultaneous linear equation is terminated by using the input unit 170. FIG. 9 illustrates the optical fluence distribution φ obtained in the present step.

Next, step of S500 of obtaining the object information by using the initial acoustic pressure distribution and the optical fluence distribution is executed. That is, the absorption coefficient distribution $\mu_a$ in the object 100 as the object information is obtained by Expression (6) and Expression (7). FIG. 10 illustrates the absorption coefficient distribution $\mu_a$ calculated in the present example.

On the other hand, as a comparison example, FIG. 11 illustrates the absorption coefficient distribution obtained in a manner that the optical fluence distribution φ is calculated by using the initial acoustic pressure distribution $\delta p_0$ by the optical diffusion equation illustrated in Expression (4), and further, the initial acoustic pressure distribution $\delta p_0$ is divided by the optical fluence distribution φ and the Gruneisen coefficient distribution Γ.

The value of the real absorption coefficient in the optical absorbent 101 is uniform as in FIG. 7. In contrast to this, the absorption coefficient in the optical absorbent 101 calculated in the present example of FIG. 10 is uniformly distributed. On the other hand, with regard to the absorption coefficient of the optical absorbent 101 obtained in the comparison example of FIG. 11, the absorption coefficient in the lower part is decreased, and it may be understood that the non-uniform absorption coefficient distribution is obtained. In addition, it may be understood that the absorption coefficient of the optical absorbent 101 illustrated in FIG. 10 is more approximated to the real value (0.24 mm$^{-1}$) than the absorption coefficient of the optical absorbent 101 illustrated in FIG. 11. That is, it may be understood that the absorption coefficient distribution obtained by the method of the present example has a higher accuracy than the absorption coefficient distribution obtained by the method of the comparison example.

According to the present example, even in a case where the photoacoustic wave that cannot be measured by the acoustic wave receiver exists, it is possible to obtain the highly accurate absorption coefficient distribution.

Example 2

According to the present example, an example in which a numeric experiment based on the second exemplary embodiment is performed will be described. The object 100 and the optical absorbent 101 to be used are similar to those in Example 1.

Figure 12:
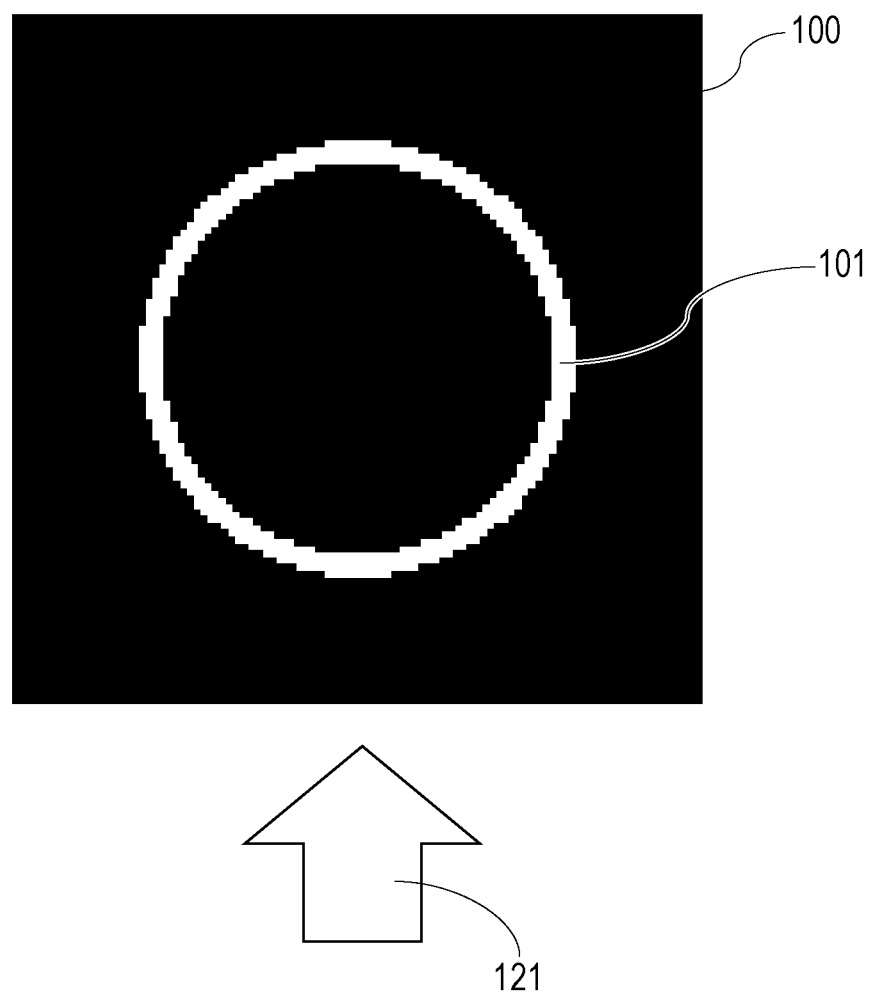
FIG. 12 illustrates a second irradiation state according to Example 2.

The present example is different from Example 1 in that two irradiation states are used. FIG. 7 and FIG. 12 illustrate a situation thereof. According to the present example, the two irradiation states including a first irradiation state in which the entire surface of the upper part of the object 100 (upper part on the paper plane) is irradiated with the light 121 as illustrated in FIG. 7 and a second irradiation state in which the entire surface of the lower part of the object 100 (lower part on the paper plane) is irradiated with the light 121 as illustrated in FIG. 12 are used.

A simulated calculation is also performed for an observation result since it is a numeric experiment this time. It is sufficient if a method similar to Example 1 may be executed for this, but since the two types of the irradiation states exist, the numeric experiment is executed in each of the irradiation states to be observed as a signal.

Next, step S2100 of obtaining the initial acoustic pressure distribution in the plurality of irradiation states is executed. For this too, a method similar to Example 1 is executed, and the initial acoustic pressure distributions $\delta p_0^{(1)}$ and $\delta p_0^{(2)}$ in the respective irradiation states are obtained.

Next, step S2200 of obtaining the background absorption coefficient distribution and the absorption coefficient distribution by using an equation representing a plurality of optical propagations corresponding to the plurality of irradiation states is executed. Herein, while the satisfaction of Expression (12) is set as the constraint, the background absorption coefficient distribution $\mu_{aB}$, the diffusion coefficient distribution D, and the absorption coefficient distribution $\delta\mu_a$ of the optical absorbent such that the objective function including the relational expression f illustrated in Expression (13) and Expression (14) is minimized are obtained. Then, a real absorption coefficient distribution $\mu_a$ is obtained by calculating a sum of the background absorption coefficient distribution $\mu_{aB}$ and the absorption coefficient of the optical absorbent 101 distribution $\delta\mu_a$.

It is noted that according to the present example, the background absorption coefficient distribution $\mu_{aB}$ and the diffusion coefficient distribution D are set as spatially uniform values. The background absorption coefficient distribution $\mu_{aB}$ and the diffusion coefficient distribution D may also have a spatial distribution. However, as the number of variables representing the spatial distributions is increased, the accuracy is further increased, but the solution technique is more complicated. Accordingly, the calculation time is also significantly increased, and therefore, the number of variables is suppressed as much as possible.

According to the present example, Gauss-Newton method is used as the method of minimizing the objective function. In addition, since it is the optimization issue with the constraint, such a method is employed that the optical fluence distributions $\varphi^{(1)}$ and $\varphi^{(2)}$ in the respective irradiation states are deleted by using the constraint illustrated in Expression (12), and a variable with which the objective function is minimized is obtained. The details will be described below.

Since Gauss-Newton method itself is in the related art, the detailed description will be omitted, but to execute the method, gradients of the objective function and the objective function and an approximate Hessian matrix of the objective function are to be performed. It is possible to obtain those when a residual $h^{(i)}$ illustrated in Expression (14) and a residual Jacobian $\partial h^{(i)}/\partial \xi$ are found. Herein ξ is an assemble of variables for convenience of the notation as defined by Expression (15) and denotes which one of variables depending on ρ.

$$\xi(\vec{\rho}) := \{\delta\mu_a(\vec{r}), \mu_{aB}, D\} \quad (15)$$

The residual $h^{(i)}$ is illustrated in Expression (14). To obtain this, $\varphi^{(i)}$ used. For that reason, $\varphi^{(i)}$ is obtained by solving Expression (12). In addition, the residual Jacobian $\partial h^{(i)}/\partial \xi$ is illustrated in Expression (16). To obtain this, $\partial \varphi^{(i)}/\partial \xi$ is used.

$$\frac{\partial h^{(i)}(\vec{r})}{\partial \xi(\vec{\rho})} = \frac{\partial \{\Gamma(\vec{r})\delta\mu_a(\vec{r})\}}{\partial \xi(\vec{\rho})} \phi^{(i)}(\vec{r}) + \Gamma(\vec{r})\delta\mu_a(\vec{r}) \frac{\partial \phi^{(i)}(\vec{r})}{\partial \xi(\vec{\rho})} \quad (16)$$

In view of the above, Expression (12) is differentiated by the variables to obtain $\partial \varphi^{(i)}/\partial \xi$. Then, Expression (17), Expression (18), and Expression (19) are established.

$$-\nabla \cdot \left\{ D \nabla \frac{\partial \phi^{(i)}(\vec{r})}{\partial \delta \mu_a(\vec{r}')} \right\} + \mu_{aB} \frac{\partial \phi^{(i)}(\vec{r})}{\partial \delta \mu_a(\vec{r}')} = 0 \quad (17)$$

$$-\nabla \cdot \left\{ D \nabla \frac{\partial \phi^{(i)}(\vec{r})}{\partial \delta \mu_{aB}} \right\} + \mu_{aB} \frac{\partial \phi^{(i)}(\vec{r})}{\partial \delta \mu_{aB}} = -\phi^{(i)}(\vec{r}) \quad (18)$$

$$-\nabla \cdot \left\{ D \nabla \frac{\partial \phi^{(i)}(\vec{r})}{\partial D} \right\} + \mu_{aB} \frac{\partial \phi^{(i)}(\vec{r})}{\partial D} = \nabla \cdot \{\nabla \phi^{(i)}(\vec{r})\} \quad (19)$$

Therefore, $\partial \varphi^{(i)}/\partial \xi$ is obtained by solving the equations in Expression (17), Expression (18), and Expression (19) to be assigned to Expression (16), and the residual Jacobian $\partial h^{(i)}/\partial \xi$ is obtained. It is noted that Expression (17) is simply solved to establish Expression (20).

$$\frac{\partial \phi^{(i)}(\vec{r})}{\partial \delta \mu_a(\vec{r})} = 0 \quad (20)$$

Accordingly, the significantly long calculation time used to solve Expression (17) is no longer needed, and also the approximate Hessian matrix of the objective function becomes a sparse matrix. Thus, a large-scale issue can also be solved by Gauss-Newton method without taking a memory restriction into account so much. This is a result of the conception by the inventor of the present invention that the transformation is performed so as to remove the variables from Expression (12) as many as possible.

In a case also where the background absorption coefficient distribution $\mu_{aB}$ and the diffusion coefficient distribution $\mu_{aB}$ are not spatially uniform but have distributions, it is possible to obtain $\partial \varphi^{(i)}/\partial \xi$ when the expression transformation is performed in a similar procedure. It is however noted that if the spatial distribution of the background absorption coefficient distribution $\mu_{aB}$ is dealt with m variables, $\partial \varphi^{(i)}/\partial \xi$ cannot be obtained unless the simultaneous linear equation equivalent to Expression (18) is solved m times. In addition, if the spatial distribution of the diffusion coefficient distribution D is dealt with the m variables, $\partial \varphi^{(i)}/\partial \xi$ cannot be obtained unless the simultaneous linear equation equivalent to Expression (19) is solved by m times. For that reason, as the number of variables representing the spatial distributions is more increased, the calculation time is further lengthened, and the number of variables is suppressed as much as possible.

Next, initial values of the variables in the optimization issue will be described. Presumable values in the object may be used as the initial values of the initial values of the background absorption coefficient distribution $\mu_{aB}$ and the diffusion coefficient distribution D. Since the background absorption coefficient distribution $\mu_{aB}$ and the diffusion coefficient distribution D can be obtained by solving this situation, those distributions may not be necessarily accurate, but roughly presumable values are used. For example, step S300 of obtaining the background absorption coefficient distribution of the object according to the first exemplary embodiment is executed, and the obtained values may be used. It is noted that according to the present example, an example in which the presumable values are twice and 0.5 times as high as the respective correct values is illustrated.

An initial value of the absorption coefficient of the optical absorbent 101 distribution $\delta \mu_a$ is obtained on the basis of Expression (12) and Expression (21).

$$\delta \mu_a(\vec{r}) = \frac{\sum_i \delta p^{(i)}(\vec{r})/\{\Gamma(\vec{r})\phi^{(i)}(\vec{r})\}}{\sum_i 1} \quad (21)$$

That is, Expression (12) is solved with respect to $\varphi^{(i)}$ by using the background absorption coefficient distribution $\mu_{aB}$ and the diffusion coefficient distribution D which are given as the initial values, and an initial value of the absorption coefficient of the optical absorbent 101 distribution $\delta \mu_a$ is obtained on the basis of Expression (21). In the case of the present example, the two type of the irradiation states exist, a sum with regard to i is taken as a sum of i=1 and i=2.

It is noted that the central difference is used for the discretization method of Expression (12). The discretization method of Expression (19) and Expression (20) is also pursuant to it. The conjugated gradient method is employed for the solution method for the simultaneous linear equation of Expression (12), Expression (18), and Expression (19) to be solved until the square norm of the residuals becomes lower than or equal to $10^{-7}$. The conjugated gradient method is also employed for the solution method for the simultaneous linear equation for defining a descent direction of the objective function until the square norm of the residuals becomes lower than or equal to $10^{-7}$. A bisection method is employed for a line search to guarantee that the objective function is decreased. It is noted that the discretization method, the solution method for the simultaneous linear equation, and the method for the line search have an arbitrary property, and the solution can be made by any method in the related art. That is, the methods according to the present example are merely examples. In addition, various techniques used for the optimization issue can be applied to the objective function illustrated in Expression (12). For example, the techniques include addition of Tikhonov regularization or Total Variation term, addition of a restriction on a solution range, and the like.

Figure 13:
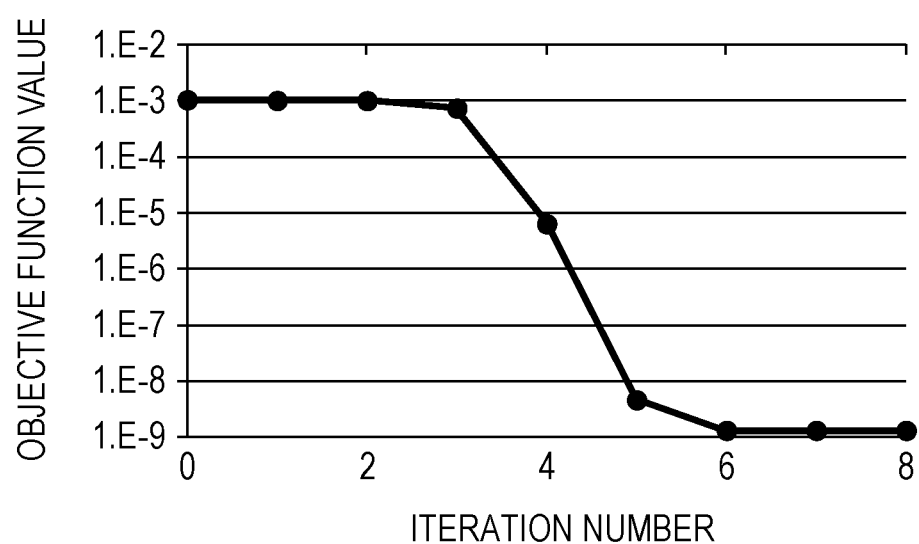
FIG. 13 illustrates an iteration number of Gauss-Newton method and an objective function value according to Example 2.

FIG. 13 is a graphic representation according to the present example. The horizontal axis represents an iteration number of the Gauss-Newton method, and the vertical axis represents a value of the objective function. In this way, when the iteration number is approximately six times, the value of the objective function is sufficiently decreased.

FIG. 14 illustrates the real absorption coefficient distribution $\mu_a$ according to the present example. The unit of the absorption coefficient in FIG. 14 is $m^{-1}$. It may be understood according to FIG. 14 that the obtained real absorption coefficient distribution $\mu_a$ is the background absorption coefficient distribution (0.0024 $mm^{-1}$) which is a value approximate to the absorption coefficient of the optical absorbent 101 (0.24 $mm^{-1}$).

According to the present example, even in a case where the accuracy of the initial value of the background absorption coefficient distribution is not sufficient as in the present example, it is possible to obtain the absorption coefficient distribution of the object at a satisfactory accuracy.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-260681, filed Dec. 17, 2013, which is hereby incorporated by reference herein in its entirety.

What is claimed is:

1. An apparatus comprising:
a light irradiation unit configured to irradiate an object with light at a plurality of timings, irradiation positions of the light with respect to the object at the plurality of timings being different from each other;
a reception unit configured to receive a photoacoustic wave generated by irradiation of the object with the light and output a plurality of received signals corresponding to the plurality of timings, wherein the reception unit has a restriction on a reception frequency band for the photoacoustic wave;
a processing unit, including a processor connected to a memory, configured to:
obtain a plurality of initial acoustic pressure distributions corresponding to the plurality of timings in the object by using the plurality of received signals;
obtain an optical fluence distribution in the object corresponding to the plurality of timings by using an equation representing propagation of the light which includes a sum of the initial acoustic pressure distribution and a correction term including a background absorption coefficient distribution of the object;
obtain the background absorption coefficient distribution and an absorption coefficient distribution of an optical absorbent in a manner that an objective function including a relational expression based on the plurality of optical fluence distributions, the absorption coefficient distribution of the optical absorbent in the object, a Gruneisen coefficient distribution in the object, and the plurality of initial acoustic pressure distributions is minimized while satisfaction of the equation representing the optical propagation is set as a constraint;
obtain object information by calculating a sum of the background absorption coefficient distribution and the absorption coefficient distribution of the optical absorbent;
output the object information to a display unit, and
cause the display unit to display an image of the object information on the display unit.

2. The apparatus according to claim 1,
wherein,
when a value of the initial acoustic pressure distribution at a position r in the object when the irradiation position is i is set as $\delta p_0^{(i)}(r)$, a value of the optical fluence distribution at the position r when the irradiation position is i is set as $\varphi^{(i)}(r)$, a value of the background absorption coefficient distribution is set as $\mu_{aB}(r)$, a value of the diffusion coefficient distribution at the position r is set as $D(r)$, a value of a Gruneisen coefficient distribution of the object at the position r is set as $\Gamma(r)$, a source term of the light at the position r is set as $s(r)$, and the absorption coefficient distribution of the optical absorbent at the position r is set as $\delta\mu_a(r)$,
while satisfaction of the equation representing the optical propagation illustrated in following Expression (1) is set as a constraint, the processing unit obtains the background absorption coefficient distribution, the diffusion coefficient distribution, and the absorption coefficient distribution of the optical absorbent with which the objective function including the relational expression f illustrated in following Expression (2) and following Expression (3) is minimized, $$-\nabla \cdot \{D(\vec{r})\nabla \phi^{(i)}(\vec{r})\} + \mu_{aB}(\vec{r})\phi^{(i)}(\vec{r}) + \delta p_0^{(i)}(\vec{r})/\Gamma(\vec{r}) = s(\vec{r}) \quad (1)$$

$$f = \sum_i \int \frac{1}{2} h^{(i)}(\vec{r})^2 d\vec{r} \quad (2)$$

$$h^{(i)}(\vec{r}) = \Gamma(\vec{r})\delta\mu_a(\vec{r})\phi^{(i)}(\vec{r}) - \delta p_0^{(i)}(\vec{r}). \quad (3)$$

3. The apparatus according to claim 2,
wherein the processing unit deletes the optical fluence distribution of Expression (3) based on Expression (1) and obtains the background absorption coefficient distribution and the absorption coefficient distribution of the optical absorbent with which the objective function including the relational expression is minimized.

4. The apparatus according to claim 1,
wherein the processing unit uses an absorption coefficient having a spatial distribution as the background absorption coefficient distribution.

5. The apparatus according to claim 1, further comprising:
an obtaining unit configured to obtain the background absorption coefficient distribution.

6. The apparatus according to claim 1,
wherein the correction term is a product of the background absorption coefficient distribution in the object, the optical fluence distribution in the object, and a Gruneisen coefficient distribution in the object.

7. The apparatus according to claim 1,
wherein the light irradiating unit includes a solid-state laser, a gas laser, a dye laser, a semiconductor laser, a laser using optical parametric oscillators, or a light emitting diode, wherein the reception unit includes a transducer using a piezoelectric phenomenon, an optical resonance, or a change in an electrostatic capacitance.

8. An apparatus comprising:
a light irradiation unit configured to irradiate an object with light;
a reception unit configured to receive a photoacoustic wave generated by irradiation of the object with the light and output a received signal, wherein the reception unit has a restriction on a reception frequency band for the photoacoustic wave;
a processing unit, including a processor connected to a memory, configured to:
  obtain an initial acoustic pressure distribution in the object by using the received signal; and
  obtain an optical fluence distribution in the object by using an equation representing propagation of the light which includes a sum of the initial acoustic pressure distribution and a correction term including a background absorption coefficient distribution of the object;
wherein,
when a value of the initial acoustic pressure distribution at a position r in the object is set as $\delta p_0(r)$, a value of the optical fluence distribution at the position r is set as $\varphi(r)$, a value of the background absorption coefficient distribution at the position r is set as $\mu_{aB}(r)$, a value of the diffusion coefficient distribution at the position r is set as $D(r)$, a value of a Gruneisen coefficient distribution in the object at the position r is set as $\Gamma(r)$, and a source term of the light at the position r is set as $s(r)$,
the processing unit
obtains the optical fluence distribution that satisfies the following expression (4), $$-\nabla \cdot \{D(\vec{r})\nabla\phi(\vec{r})\}+\{\delta p_0(\vec{r})+\Gamma(\vec{r})\mu_{aB}(\vec{r})\phi(\vec{r})\}/\Gamma(\vec{r})=s(\vec{r}) \quad (4),$$

obtains object information by using the initial acoustic pressure distribution and the optical fluence distribution;

outputs the object information to a display unit, and causes the display unit to an image of the object information.

9. The apparatus according to claim 1, wherein the processing unit uses an absorption coefficient having a uniform value as the background absorption coefficient distribution.

10. The apparatus according to claim 9, wherein the processing unit uses an average absorption coefficient of the object as the background absorption coefficient distribution.

11. The apparatus according to claim 8, wherein the processing unit uses an absorption coefficient having a uniform value as the background absorption coefficient distribution.

12. The apparatus according to claim 11, wherein the processing unit uses an average absorption coefficient of the object as the background absorption coefficient distribution.

13. The apparatus according to claim 8, wherein the processing unit uses an absorption coefficient having a spatial distribution as the background absorption coefficient distribution.

14. The apparatus according to claim 8, further comprising:
an obtaining unit configured to obtain the background absorption coefficient distribution.

15. The apparatus according to claim 8, wherein the correction term is a product of the background absorption coefficient distribution in the object, the optical fluence distribution in the object, and a Gruneisen coefficient distribution in the object.

16. The apparatus according to claim 8, wherein the light irradiating unit includes a solid-state laser, a gas laser, a dye laser, a semiconductor laser, a laser using optical parametric oscillators, or a light emitting diode,
wherein the reception unit includes a transducer using a piezoelectric phenomenon, an optical resonance, or a change in an electrostatic capacitance.

* * * * *